US00PP10937P

United States Patent [19]

Schuurman

[11] Patent Number: Plant 10,937

[45] Date of Patent: Jun. 1, 1999

[54] FLORIBUNDA ROSE PLANT NAMED 'SUNPETE'

[75] Inventor: Frank Schuurman, Whenuapai, New Zealand

[73] Assignee: DeVor Nurseries, Inc., Watsonville, Calif.

[21] Appl. No.: 08/859,580

[22] Filed: May 20, 1997

[51] Int. Cl.[6] ..... A01H 5/00

[52] U.S. Cl. ..... Plt./151

[58] Field of Search ..... Plt./28, 29, 150, Plt./151, 129

[56] References Cited

PUBLICATIONS

UPOV-ROM, Jan. 1998, Plant variety Database, GTI Jouve Retrieval Software, citations for 'Sunpete'.

*Primary Examiner*—Howard J. Locker
*Attorney, Agent, or Firm*—Christie, Parker & Hale, LLP

[57] ABSTRACT

A floribunda rose variety producing bright red flowers.

1 Drawing Sheet

BACKGROUND OF THE INVENTION

The present invention relates to a new and distinct floribunda rose variety which was originated by my crossing as seed parent the variety known as 'Pink Delight' and as pollen parent the variety known as 'Dicky Bird.' The varietal denomination of this new rose is 'Sunpete.'

SUMMARY OF THE INVENTION

Among the novel characteristics possessed by the new variety which distinguish it from its parents and all other varieties of which I am aware are its attractive, many-petaled, bright red flowers borne on a bushy, vigorous plant.

Asexual reproduction by budding of the new variety as performed in Watsonville, Calif., shows that the foregoing and other distinguishing characteristics come true to form and are established and transmitted through succeeding propagations. Other known forms of asexual reproduction for roses may be also employed.

COMPARISON WITH PATENTS

The new variety differs from 'Pink Delight' and 'Dicky Bird' in that 'Pink Delight' has pink blooms and 'Dicky Bird' is an orange flowered hybrid tea, whereas the new variety is a red flowered floribunda.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

BRIEF DESCRIPTION OF THE NEW VARIETY

Parentage: Seedling.

*Seed parent.*—'Pink Delight'.

*Pollen parent.*—'Dicky Bird'.

Class: Floribunda.

The following is a detailed description of the new variety, from specimens grown under glass in Watsonville, Calif., in the month of September. The color terminology used is in accordance with The Royal Horticultural Society Colour Chart (RHSCC), and refers to plate numbers in the aforementioned color chart. Phenotypic expression may vary depending on light, environmental and cultural conditions.

1. FLOWER

Blooming Habit: Continuous.

A. Bud:

(1) *Size.*—Small.

(2) *Form.*—Pointed.

(3) *Color.*—Green bud near 144A; When sepals first divide, bud color is near 187C.

(4) *Sepals.*—Sepals cover bud, becoming horizontal at maturity; leaf-shaped ends, foliaceous, about 2.5 to 3cm long. Color: Near 144A.

(5) *Peduncle.*—Length: About 5 cm to about 7 cm. Aspect: Rough. Strength: Slender. Color: Near 144A.

(6) *Bracts.*—None.

B. Bloom:

(1) *Size.*—Average size when fully expanded—about 6 cm to about 7 cm.

(2) *Borne.*—Clusters of 3 to 5 blooms.

(3) *Form.*—Imbricated, slightly cupped, outer petals curl under.

(4) *Petalage.*—Number of petals under normal conditions—about 62 to 75.

(5) *Color* (⅓–½ *open*).—Outer petals—Top surface: near 46A. Undersurface: near 63A. Inner petals—Top surface: near 46A. Undersurface: near 60B. Base of petals: Near 2B. General tonality from a distance: Red.

(6) *Color* (*fully open*).—Outer petals—Top surface: near 46B. Undersurface: near 53C. Inner petals—Top surface: near 46C. Undersurface: near 53D. Base of petals: Near 2D. General tonality at a distance: Red.

(7) *Color change.*—Bloom really does not lighten, but it becomes a duller red. Petal top surface: near 46C. Petal undersurface: near 53D. Base of petals: Near 2D. General tonality at a distance: Red.

C. Petals:

(1) *Texture.*—Thick, smooth.

(2) *Appearance.*—Inside velvety and outside matte.

(3) *Form.*—Broadly Elliptic, outer edges roll under and quill.

(4) *Arrangement.*—Imbricated.

(5) *Petaloids.*—Many, about 16 to 20.
(6) *Persistence.*—Petals drop off cleanly.
(7) *Fragrance.*—Very slight fruity fragrance.
(8) *Lasting quality.*—On plant about 7 to 8 days; about 8 to 10 days after cutting.

2. REPRODUCTIVE ORGANS

A. Stamens:
(1) *Arrangement.*—Irregularly arranged around styles.
(2) *Stamens.*—Anthers: Color—near 22B. Filaments: Color—near 1B.
(3) *Pollen.*—Color—near 22B.

B. Pistils:
(1) *Styles.*—Thin, very long, about 0.08 cm above stamens.
(2) *Stigmas.*—Color—near 15D.

C. Characteristics of hips: None observed.

3. PLANT

A. Form: Compact, upright, height about 57 to 60 cm and spread about 26 to 30 cm, at first season.
B. Growth: Vigorous.
C. Foliage: Compound 3 to 5 leaflets.
(1) *Size.*—Small.
(2) *Quantity.*—Abundant.
(3) *Color.*—New foliage—upper side near 147A, underside near 147B with tinges of near 183C; mature foliage—upper side near 147A, underside near 147B.
(4) *Shape.*—Oval with rounded base.
(5) *Texture.*—Upper side leathery, semi-glossy; underside leathery, veiny.
(6) *Edge.*—Serrate.
(7) *Serration.*—Double Denticulate.
(8) *Leaf stem.*—Color—medium green.
(9) *Stipules.*—Adnate with enlarged middle, slightly bearded, curving downward.
(10) *Rachis.*—Small prickles underneath.
(11) *Petioles.*—Top near 146A, underside near 144B.
(12) *Auricle.*—Long, medium margins slightly bearded, curving outward.
(13) *Resistance to disease.*—Very resistant to mildew, rust and blackspot.

D. Wood:
(1) *New wood.*—Color near 146B, bark smooth.
(2) *Old wood.*—Color near 146A, bark smooth.

E. Flower Stem: About 40 cm to about 51 cm from last cut.
F. Thorns:
(1) *Thorns.*—None, very few prickles.

G. Winter hardiness: Winter hardy in Watsonville, Calif.

I claim:

1. A new and distinct floribunda rose plant of the variety substantially as shown and described.

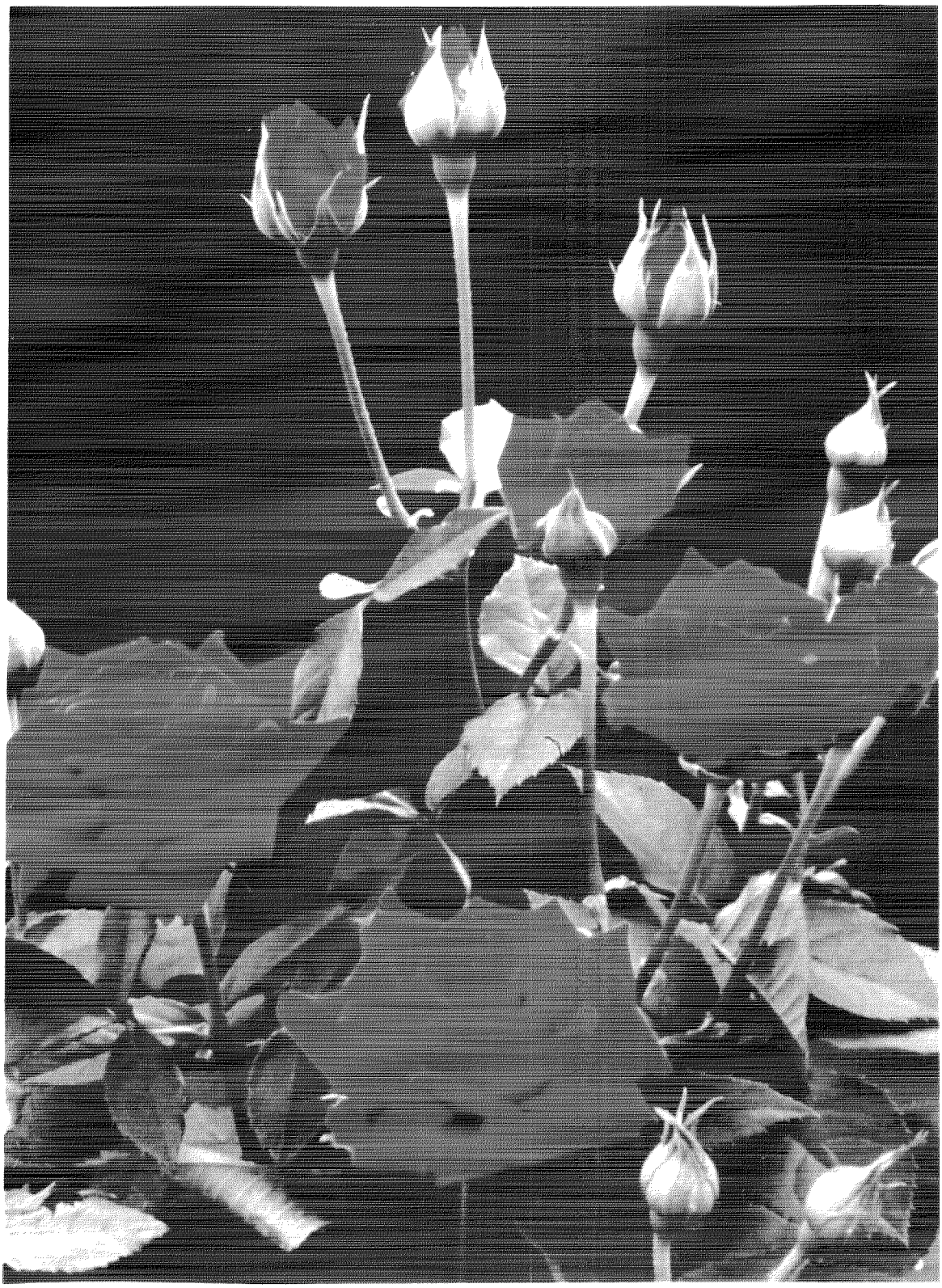

* * * * *